United States Patent [19]

Koga et al.

[11] Patent Number: 4,461,017
[45] Date of Patent: Jul. 17, 1984

[54] FLUORESCENT X-RAY DEVICE

[75] Inventors: Toshiyuki Koga; Hiroshi Ishijima, both of Tokyo, Japan

[73] Assignee: Seiko Instruments & Electronics Ltd., Tokyo, Japan

[21] Appl. No.: 343,199

[22] Filed: Jan. 27, 1982

[30] Foreign Application Priority Data

Feb. 4, 1981 [JP] Japan ............................. 56-14677[U]

[51] Int. Cl.³ ...................... G01N 23/223; H05G 1/02
[52] U.S. Cl. ..................................... 378/044; 378/206
[58] Field of Search ................... 378/205, 206, 44, 50, 378/45

[56] References Cited

U.S. PATENT DOCUMENTS 1,976,179 10/1934 Mannl ................................. 378/206
2,474,421 6/1949 Hollstein ............................. 378/206
4,178,513 12/1979 Dubois et al. .......................... 378/44

*Primary Examiner*—Alfred E. Smith
*Assistant Examiner*—T. N. Grigsby
*Attorney, Agent, or Firm*—Robert E. Burns; Emmanuel J. Lobato; Bruce L. Adams

[57] ABSTRACT

A flourescent x-ray device for irradiating x-rays to a sample so that flourescent x-rays emitted from the sample can be detected is described. A stationary fixed collecting plate is used instead of the movable reflecting plate employed in the prior art. The reflecting plate possesses the characteristics of being transmissive to x-rays and being reflective to visible light so that an image of the sample can be viewed by an observer and the sample can be irradiated with x-rays passing through the plate. The invention permits a remarkable decrease in manufacturing cost. Moreover, the device can be operated in a stable condition with high accuracy for a long time.

7 Claims, 3 Drawing Figures

FLUORESCENT X-RAY DEVICE

BACKGROUND OF THE INVENTION

The present invention relates to a fluorescent X-ray device, and more particularly to an improved device which enables an observer to observe a place the where X-ray applied to irradiate a sample from a position overhead of the sample and to increase the accuracy of measurment.

In the prior art devices which have been used, as illustrated in FIGS. 1 and 2, a movable reflecting plate 1 is provided and the reflecting plate 1 is made of glass. When the X-ray is to be actually applied to a sample 5 from an X-ray tube 2, the reflecting plate 1 is moved by a rotary-solenoid 3 to another position, as shown in FIG. 2, so that the X-ray can be passed therethrough.

However according to the conventional arrangement described above, in order to apply the X-ray to the sample 5, it is necessary that the reflecting plate 1 be moved by the rotary-solenoid 3 and a collimator 4 must be moved to the position through where the X-ray is passed, prior to applying the X-ray to the sample 5. Therefore, the cost of the device is increased due to the moving device, and moreover, prolonged use causes the position of the collimator to vary so that an adjusting device for correcting the displacement of the collimator is needed.

SUMMARY OF THE INVENTION

An object of the present invention is to provide an effective device for eliminating the foregoing drawbacks and such is achieve by providing a reflecting plate between a collimator and a sample and the reflecting plate is made of the material which reflects light and allows to the X-ray pass therethrough.

DETAILED DESCRIPTION OF THE INVENTION

Figure 1:
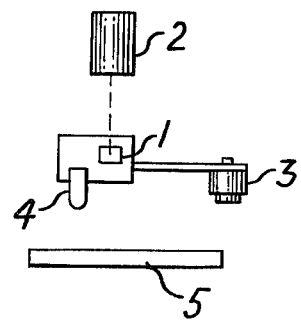
FIGS. 1 and 2 are explanatory views of a conventional fluorescent X-ray device and FIG. 3 is an explanatory illustrating a fluorescent X-ray device of the present invention.
Figure 2:
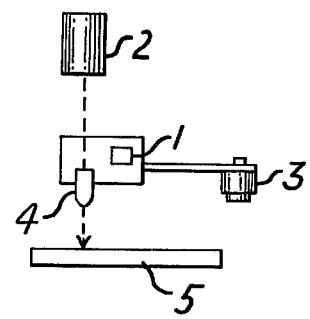
Figure 3:
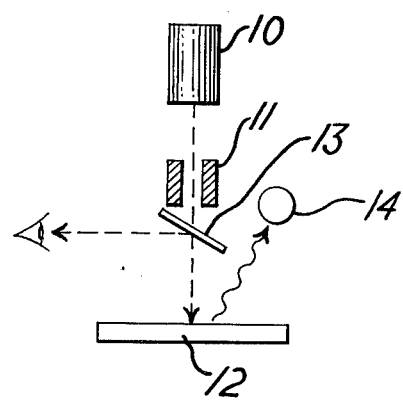

A fluorescent X-ray device of the present invention will be described in more detail in conjunction with FIG. 3. The reference number 10 designates an X-ray tube under which a collimator 11 is arranged. The collimator collimates the X-rays into an X-ray beam and directs the beam along an X-ray path to irradiate a sample 12. Between the collimator 11 and the sample 12, a reflecting plate member 13 which is especially developed for the present invention is stationarily fixed to a base (not shown). The reflecting plate 13 is made of a material which reflects light but allows X-rays to pass, for example, the reflecting plate 13 can be constructed by plating $SiO_2$ or an organic film with aluminum, or by evaporation to obtain a reflecting surface. By such a construction, X-rays from the X-ray tube 10 are applied to the sample 12 through the reflecting plate 13 and the fluorescent X-rays emitted from the sample 12 are detected by a detecting device 14. In this case, since visible light from the sample is reflected by the reflecting plate 13, the condition and location of the sample 12 can be viewed or observed by, an observer for example, through a microscope (not shown).

Therefore, according to the present invention, no moving means is required as in the prior art since the reflecting plate is fixed and thus a remarkable decrease in the manufacturing cost can be attained. Moreover, even if the device is used for a long time, the device can be operated in a stable condition with high accuracy due to the reflecting plate being stationarily fixed.

We claim:

1. In a fluorescent X-ray device for irradiating a sample with X-rays: an X-ray tube for emitting X-rays; collimating means for collimating the X-rays into an X-ray beam and directing the X-ray beam along an X-ray path to a sample; reflecting means stationarily disposed along the X-ray path downstream of the collimating means and composed of a material which effectively transmits therethrough the X-ray beam to enable the sample to be irradiated with X-rays and which effectively reflects visible light reflected by the sample to enable an image of the sample to be viewed by an observer; and detecting means for detecting fluorescent X-rays emitted from the sample.

2. A device according to claim 1; wherein the reflecting means comprises a plate member fixedly mounted at a predetermined angle with respect to the X-ray path.

3. A device according to claim 2; wherein the plate member comprises $SiO_2$.

4. A device according to claim 2; wherein the plate member comprises an organic film plated with aluminum.

5. A device according to claim 1; wherein the reflecting means comprises a plate member fixedly mounted at a predetermined angle with respect to the X-ray path to reflect the image of the sample incident thereon from along the X-ray path to a remote point for viewing by an observer.

6. A device according to claim 5; wherein the plate member comprises $SiO_2$.

7. A device according to claim 5; wherein the plate member comprises an organic film plated with aluminum.

* * * * *